(12) United States Patent
Harper et al.

(10) Patent No.: US 10,475,530 B2
(45) Date of Patent: Nov. 12, 2019

(54) SYSTEM AND METHOD FOR ACTIVATION AND DEACTIVATION OF CUED HEALTH ASSESSMENT

(71) Applicant: Sonde Health, Inc., Boston, MA (US)

(72) Inventors: James D Harper, Boston, MA (US); Michael Chen, Norwood, MA (US)

(73) Assignee: Sonde Health, Inc., Boston, MA (US)

( * ) Notice: Subject to any disclaimer, the term of this patent is extended or adjusted under 35 U.S.C. 154(b) by 19 days.

(21) Appl. No.: 15/809,312

(22) Filed: Nov. 10, 2017

(65) Prior Publication Data

US 2018/0240535 A1 Aug. 23, 2018

Related U.S. Application Data

(60) Provisional application No. 62/420,340, filed on Nov. 10, 2016.

(51) Int. Cl.
| | |
|---|---|
| *G10L 15/00* | (2013.01) |
| *G16H 10/20* | (2018.01) |
| *G10L 17/26* | (2013.01) |
| *G10L 15/22* | (2006.01) |
| *G16H 50/30* | (2018.01) |
| *G10L 17/00* | (2013.01) |
| *G10L 25/78* | (2013.01) |
| *G10L 25/66* | (2013.01) |

(Continued)

(52) U.S. Cl.
CPC ........... *G16H 10/20* (2018.01); *A61B 5/4803* (2013.01); *G10L 15/22* (2013.01); *G10L 17/005* (2013.01); *G10L 17/26* (2013.01); *G10L 25/66* (2013.01); *G10L 25/78* (2013.01);

*G16H 50/20* (2018.01); *G16H 50/30* (2018.01); *A61B 5/16* (2013.01); *A61B 5/4806* (2013.01)

(58) Field of Classification Search
CPC ....... A61B 5/0022; A61B 5/16; A61B 5/4803; A61B 5/749; A61B 5/7264; G06F 19/3418; G16H 10/60; G10L 15/00; G10L 17/005; G10L 25/00; G10L 25/48; G10L 25/63

See application file for complete search history.

(56) References Cited

U.S. PATENT DOCUMENTS

| | | | | |
|---|---|---|---|---|
| 5,357,427 A | * | 10/1994 | Langen | ............... G06F 19/3418 600/300 |
| 9,579,056 B2 | * | 2/2017 | Rosenbek | ............ A61B 5/4082 |

(Continued)

OTHER PUBLICATIONS

Muhammad, G. (2015). Automatic speech recogitio usig iterlaced derivative patter for cloud based healthcare system. Cluster Computing, 18(2), 795-802.*

(Continued)

*Primary Examiner* — Edgar X Guerra-Erazo
(74) *Attorney, Agent, or Firm* — Ashok Tankha

(57) ABSTRACT

A system for activating a cued health assessment, which includes an audio receiver for receiving voice samples to measure one of a plurality of voice biomarkers, an audio processing module for extracting one of a plurality of biomarkers from the received voice samples, the audio processing module further classifies the received voice samples to one of plurality of predetermined health states according to the extracted biomarkers, and a voice sample scheduler for activating a cued health assessment module when the classified health state is a clinically actionable health state.

20 Claims, 5 Drawing Sheets

(51) Int. Cl.
*A61B 5/00* (2006.01)
*G16H 50/20* (2018.01)
*A61B 5/16* (2006.01)

(56) References Cited

U.S. PATENT DOCUMENTS

| | | | | |
|---|---|---|---|---|
| 2003/0078515 | A1* | 4/2003 | Menzel | A61B 5/0002 |
| | | | | 600/559 |
| 2006/0129390 | A1* | 6/2006 | Kim | G10L 17/26 |
| | | | | 704/220 |
| 2010/0292545 | A1* | 11/2010 | Berka | A61B 5/048 |
| | | | | 600/301 |
| 2011/0087079 | A1* | 4/2011 | Aarts | A61B 7/003 |
| | | | | 600/300 |
| 2012/0265024 | A1* | 10/2012 | Shrivastav | A61B 5/40 |
| | | | | 600/300 |
| 2017/0053665 | A1* | 2/2017 | Quatieri, Jr. | G10L 25/27 |
| 2017/0076740 | A1* | 3/2017 | Feast | G10L 25/63 |
| 2017/0119302 | A1* | 5/2017 | Rosenbek | A61B 5/4082 |
| 2017/0125034 | A1* | 5/2017 | Kakadiaris | G06F 3/165 |

OTHER PUBLICATIONS

Vacher, M., Serignat, J. F., Chaillol, S., Istrate, D., & Popescu, V. (Sep. 2006). Speech and sound use in a remote monitoring system for health care. In International Conference on Text, Speech and Dialogue (pp. 711-718). Springer, Berlin, Heidelberg.*

* cited by examiner

SYSTEM AND METHOD FOR ACTIVATION AND DEACTIVATION OF CUED HEALTH ASSESSMENT

CROSS REFERENCE TO RELATED APPLICATIONS

This application claims the benefit of the filing date of U.S. Provisional Patent Application 62/420,340, entitled "SYSTEM AND METHOD FOR ACTIVATION AND DEACTIVATION OF CUED HEALTH ASSESSMENT" to James D. Harper, which was filed on Nov. 10, 2016, the disclosure of which is hereby incorporated entirely herein by reference.

TECHNICAL FIELD

The present invention relates to intelligent assistants. More specifically, embodiments of the present invention relate to intelligent automated assistants that can be used to perform a health assessment by collecting and analyzing a voice sample.

BACKGROUND

Digital health assessments are conventionally gathered with survey instruments, or health screening devices, e.g. stethoscopes, blood pressure and heart rate monitors. In this cued mode, a patient is prompted, or cued, to put on a device to allow for measurements of physiological biomarkers to take place, or to answer a predetermined set of questions to collect contextual health information.

There is a need for better timing of the activation or application of such assessment tools. Similarly, there is a need for better timing of the deactivation of such assessment tools, in order to minimize user boredom, fatigue, and apathy, or other undesirable usability impacts.

Today's electronic devices are able to access a large, growing, and diverse quantity of functions, services, and information, both via the Internet and from other sources. Functionality for such devices is increasing rapidly, as many consumer devices, smartphones, tablet computers, and the like, are able to run software applications to perform various tasks and provide different types of information. Increasingly, these devices have become the hub for managing important health data. They run a range of independent health applications and interface with a range of wearable and clinical sensing devices. While these apps and devices can be important tools in systems designed to monitor and improve individual health, each one has different interfaces and interaction needs and schedules that need to be engaged regularly for maximum benefit. Many of these interactions can be burdensome and become overwhelming or frustrating for users in ways that lead to decreased utilization of the tools or lack of awareness when input is needed or helpful information is available.

In particular, individuals who are impaired or disabled in some manner, and/or are elderly, young, unfamiliar with a device, busy, distracted, and/or operating a vehicle may have difficulty interfacing with their electronic devices effectively, and/or engaging online services effectively. Such users are particularly likely to have difficulty with the large number of diverse and inconsistent health functions, applications, and websites that may be available for their use.

Additionally, individuals who consider themselves healthy may be less likely or inclined to initiate use of health monitoring and screening applications or features that could help anticipate and even prevent potential medical problems.

SUMMARY

The present invention provides a system for activating a cued health assessment. The system includes an audio receiver for receiving voice samples to measure one of a plurality of voice biomarkers, and an audio processing module for extracting one of a plurality of biomarkers from the received voice samples. The audio processing module further classifies the received voice samples to one of plurality of predetermined health states according to the extracted biomarkers. The system also includes a voice sample scheduler for activating a cued health assessment module when the classified health state is a clinically actionable health state.

The present invention also provides a method of activating a cued health assessment. The method includes a step of receiving voice samples from a continuous voice collection device, and extracting one of a plurality of biomarkers from the received voice samples. The method further includes a step of classifying the received voice samples to one of plurality of predetermined health states according to the extracted biomarkers. Finally, the method includes a step of activating a cued health assessment module when the classified health state is a clinically actionable health state.

DETAILED DESCRIPTION

Figure 1:
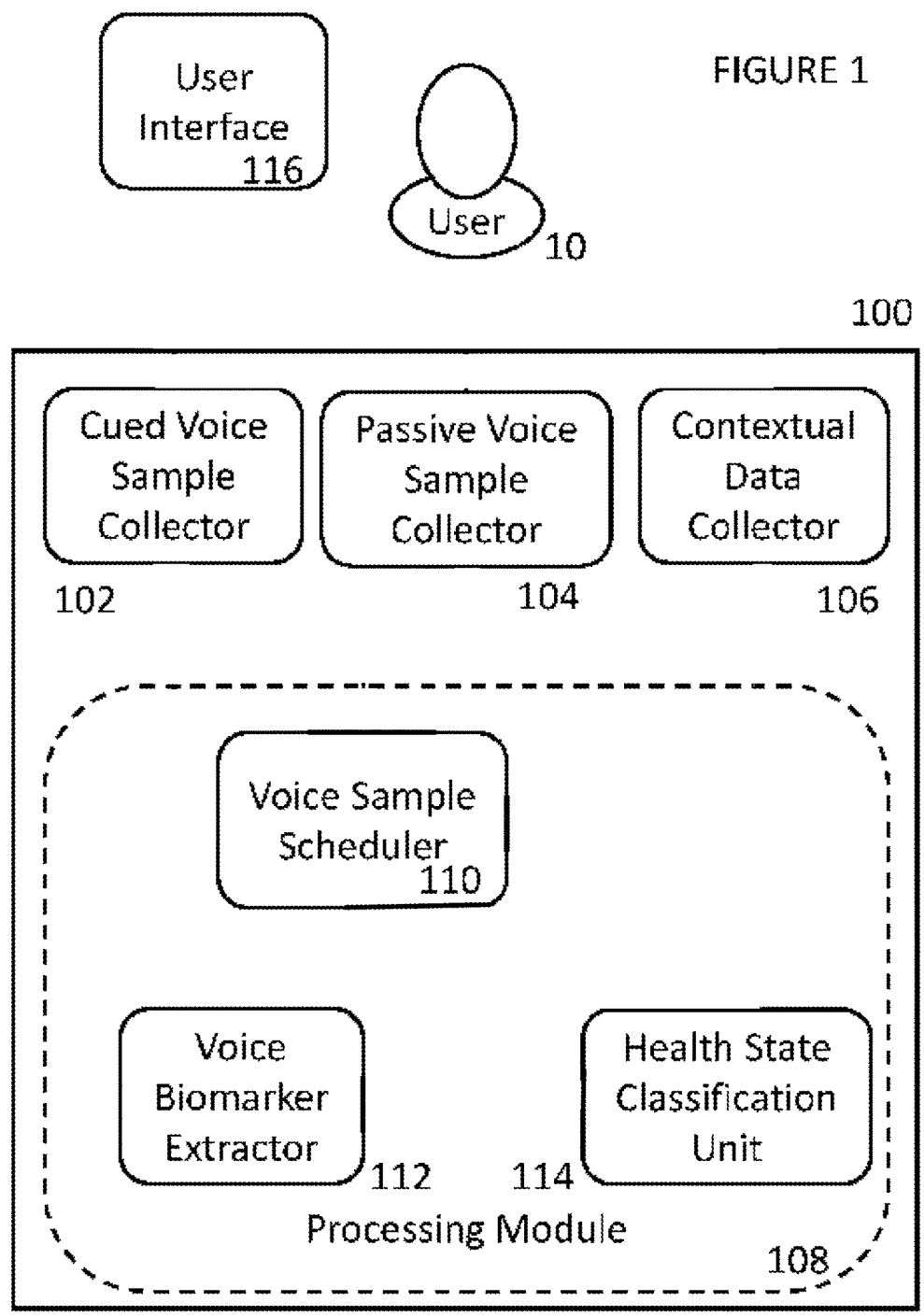
FIG. 1 depicts a system for activating a cued health assessment according to an embodiment of the present inventions.

Non-linguistic cues are superior for guiding the activation of digital health related services. Aspects of systems and methods for service activation using non-linguistic cues have been described in co-pending application (U.S. application Ser. No. 15/484,610 titled "System and method for activation of voice interactive services based on user state") and is incorporated herein by reference and in parts. Reducing the delay between a change in health status and making accurate information characterizing that change available to patients and the people or services coordinating their health care is a very important pre-requisite for enabling earlier intervention and improved treatment outcomes across a wide range of health conditions. Because user-generated requests represent only a small fraction of user-generated sounds containing potential health information made by an individual near an audio data collector, the potential to monitor all audio produced by an individual not limited by inclusion of a key word or phrase or understandable user request allows significantly increased monitoring frequency and reduced latency for health information. For health applications dependent on detecting and measuring rapidly improving or declining health states such as development of novel fast-acting depression therapeutics and detection of neurological conditions such as epilepsy and stroke with rapid episodic onset, analysis of user generated requests would not have sufficient measurement frequency to provide meaningful responses on timeframes relevant to the condition. Importantly, simple solutions where audio data collectors are always on and analyzing linguistic content of incoming user-generated-audio will be impractical in many health monitoring embodiments that rely on battery power or that would benefit from increased levels of user privacy. In these cases having an always-on health activity detection capability that is analogous to voice activity detection capabilities allow analysis and storage of health-related acoustic information that can much more efficiently manage power, computational, and storage resources and does not require full waveform recording or storage of linguistic content that may contain sensitive or private user-content and will have increased amounts of identifying information.

Methods, systems, and computer readable storage medium related to operating an intelligent and context-aware automated assistant are disclosed herein. A user request is received through an interactive voice interface of the intelligent context-aware assistant, the user request including at least an audio or speech input received from a user. One or more candidate mental or physical health domains relevant to the user request are identified from a plurality of predefined health domains, where each predefined domain presents a respective area of service offered by the context-aware intelligent automated assistant, and the identifying is based on respective degrees of match between contextual states of the user estimated from non-linguistic or paralinguistic features of audio or speech and contextual states associated with each predefined domain. Feedback is provided to the user through the conversation interface of the intelligent automated assistant, where the feedback presents a description of the contextual state detected and elicits additional input from the user to further estimate the contextual state, specifies one or more parameters associated with a particular candidate domain relevant to that state, shares information and data about that health state with one or more users or health care providers, and/or schedules appointments or pre-defined services to further diagnose, monitor, or treat the health state.

Activation of existing voice interactive systems is achieved either through physical manipulation of the device (e.g. a button push) or via passive pattern-matching analysis of voice to detect certain words or phrases that a system is pre-configured or trained to recognize as activation commands. Such keyword or pass-phrase controlled systems that use only linguistic content for control require significant effort to be retrained for different languages, and produce a relatively unnatural and limited set of interaction possibilities that respond poorly to changing context. The use of non-linguistic vocal features to activate the system can enable a much broader and richer interaction interface and creates the possibility for a range of additional functions for voice interactive devices beyond semantic control and responses.

Activation of a system based on detection of specific affect or mood in the voice of an individual in the room could automatically activate the system and direct it to produce a system response appropriate to the state of the individual, as follows:

If sadness or negative affect is detected, system could take actions including ask if they are feeling down, asking if they would like to talk to a friend or family member, and/or ask whether the user wants to play music that has positive lyrics or a major chord progression, etc. (can initiate the music automatically or can adjust a playlist already in progress to change the emotional valence).

If the user is anxious, the system could detect that state, activate, and play soothing music or select from a predetermined list of activities designed to engage the user in ways that reduce the ability of the individual to focus on the source of the anxiety.

If an argument is detected the system could detect the conflict and anger in speech among multiple users and activate to initiate a predetermined set of actions in response to that situation (record the time and identity of the participants, determine the topic of the argument and respond in a contextually aware manner, initiate activity of a baby monitor or a recording system based on pre-configured system settings (e.g. for detecting verbal abuse by a childcare worker), etc.

If the system detects confusion, it could activate and ask the user if he or she would like any help.

Embodiments of present invention can further include activation of the system based on the health or physiological state of the user's states relating to Depression, Parkinson's or other diseases. Embodiments of present invention can be integrated with other sensors. To further ensure that the detected state is accurately attributed to a specific individual the present invention can be integrated with biometric identification of one or more individuals who speak near the device via analysis of the same voice sample used to assess speaker state or intent or via inputs from other integrated sensors. Embodiments of the present invention can be directed to detect dementia associated loss of direction, etc.

According to embodiments of the present invention, a cued health assessment activation system is provided that include two sequential stages. An exemplar first stage includes an audio data collector that collects a voice sample from a user.

An exemplar second stage that includes a processing module that performs three main functions: 1) processes the audio or voice sample to extract features to classify a user state, 2) classifies a user voice sample to a predetermined health or physiological state, and 3) activates a cued health assessment or a passive health assessment based on the predetermined health or physiological state.

Conventional methods for analyzing a voice audio sample for user states can be provided to classify a plurality of predetermined user states. For example, states or status in depression, anhedonia and other sub-symptoms of Major Depressive Disorder (MDD) may be detected based on vocal biomarkers described in Vocal and facial biomarkers of depression based on motor incoordination and timing (James R. Williamson et al.). Another set of features and classification methods can be found in concurrently pending U.S. patent application Ser. No. 15/464,756, filed on Mar. 21, 2017. As another example, states or status of cognitive impairment may be detected based on vocal biomarkers described in Cognitive impairment prediction in the elderly based on vocal biomarkers (Bea Yu et al.).

As another example, states or status of cognitive load may be detected based on vocal biomarkers described in Vocal biomarkers to discriminate cognitive load in a working memory task. (Thomas F. Quatieri et al.), and Cognitive load classification using formant features (Tet Fei Yap et al.).

As another example, states or status of Alzheimer's disease and dementia may be detected based on vocal biomarkers described in Automatic speech analysis for the assessment of patients with predementia and Alzheimer's disease (Konig et al.)

As another example, states or status of Parkinson disease (PD) may be detected based on vocal biomarkers described in Segment-dependent dynamics in predicting Parkinson's disease (James R. Williamson et al.)

As another example, states or status of Amyotrophic Lateral Sclerosis disease (ALS) may be detected based on vocal biomarkers described in Relation of automatically extracted formant trajectories with intelligibility loss and speaking rate decline in Amyotrophic Lateral Sclerosis (Rachelle L. Horwitz-Martin et al.)

As another example, states or status of Coughing frequency and severity may be detected based on vocal biomarkers described in An update on measurement and monitoring of cough: what are the important study endpoints (Arietta Spinou et al.).

As another example, states or status of stress may be detected based on vocal biomarkers described in Vocal indices of stress: a review (Cheryl L. Giddens et al.).

As another example, states or status of TBI and concussion symptoms may be detected based on vocal biomarkers described in Voice and ocular dynamics in classifying cognitive change with preclinical mTBI (Brian Helfer et al.).

As another example, states or status of Chronic Obstructive Pulmonary Disease (COPD) may be detected based on vocal biomarkers described in Voice Analysis in individuals with chronic obstructive pulmonary disease (Anuradha Shastry et al.).

As another example, states or status of user emotion and affect may be detected based on acoustic features described in Recognising Realistic Emotions and Affect in Speech: State of the Art and Lessons Learnt from the First Challenge (Bjorn Schuller et al.), and Long term suboxone emotional reactivity as measured by automatic detection in speech (Edward Hill et al.) Similarly, states or status of confusion, agitation, sleepiness, anxiety, breathlessness, respiration rate, fluid retention, congestive heart disease, hypoglycemia, hypertension or hypotension, asthma, respiratory viral infection, influenza infection, Multiple Sclerosis (MS), Schizophrenia may be detected.

As shown in FIG. 1, an embodiment of the present invention provides a system 100 for activating a cued health assessment according to a classified health state or a status of a user 10. The system 100 includes a cued voice sample collector 102 adapted to collect a sample of speech, and a passive voice sample collector 104 adapted to contiguously collect samples of speech, a processing module 108 including a voice biomarker extractor 112 and a health state classification unit 114, and a voice sample scheduler (cued assessment activator) 110. The voice biomarker extractor 112 extracts a plurality of acoustic features from the sample of speech, and the classification unit 114 classifies a user state or status from the plurality of acoustic features. From the classified user state or status, the voice sample scheduler/activator 110 activates a cued health assessment or a passive health assessment for the user.

As shown in FIG. 1, the system 100 can further couple with a contextual data collector 106 and a user interface device 116 to collect additional contextual health data from user 10. The performance of system 100 can be furthermore improved by the contextual data such as those activity measurements obtained from accelerometers, light sensors, screen use and interaction data, and phone call, messaging, or data use.

Embodiments of the present invention provides several advantages over existing digital health assessments performed by interactive digital assistants. For example, when the user health status is classified to be generally health, a passive health assessment is activated or scheduled so that the user is not fatigued by the cued health assessment exercises.

Figure 2:
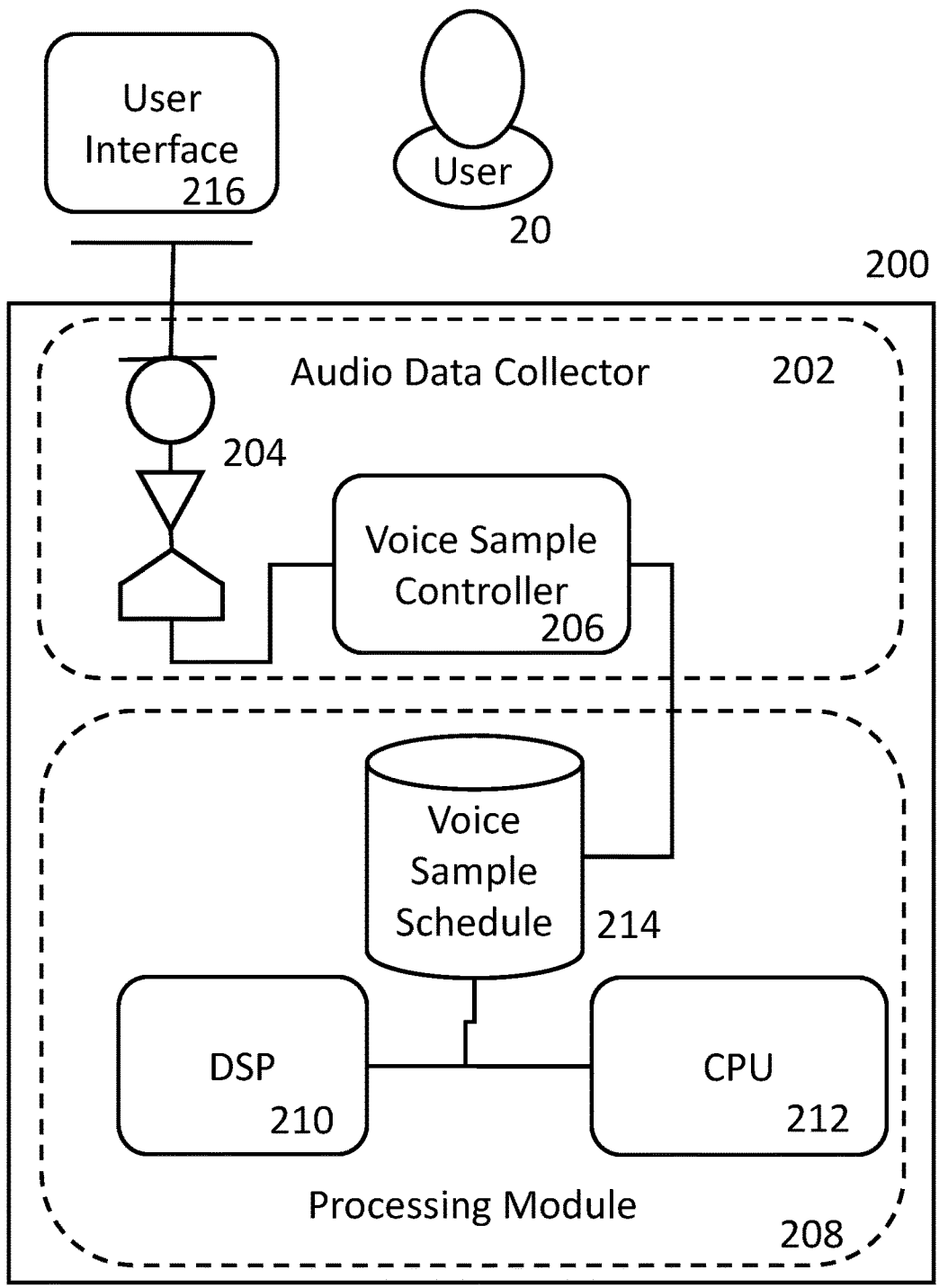
FIG. 2 depicts a system for activating a cued health assessment according to another embodiment of the present inventions.

The audio data collector 202 can be embodied with a microphone module 204 and a voice sampling controller 206, as shown in FIG. 2. According to an embodiment of the present invention, the microphone module 204 includes a microphone for converting an acoustic energy into a voltage signal. The microphone module 204 also includes an operational amplifier coupled to the microphone for amplifying the voltage signal. And the microphone module 204 includes an analog-to-digital converter for converting the voltage signal into digital data.

Also shown in FIG. 2, is an embodiment of the processing module 208. According to an embodiment of the present invention, the processing module 208 includes a digital signal processor 210. The digital signal processor can be coupled to the audio data collector 202 to extract the plurality of acoustic features from the sample of speech. In other words, when the digital signal processor 210 executes a stored instruction set, it performs the functions of the voice biomarker extractor 112 (see FIG. 1). The processing module also includes a general-purpose processor 212. The general-purpose digital processing can be coupled to an output of the digital signal processor 210 (see voice biomarker extractor 112 in FIG. 1) to receive the plurality of acoustic features and classifies the sample of speech to a predetermined status of the user. In other words, when the general-purpose processor 212 executes a stored instruction set, it performs the functions of the classification unit 114 and the functions of the health assessment (cued or passive) activator and scheduler 110 (see FIG. 1).

Figure 3:
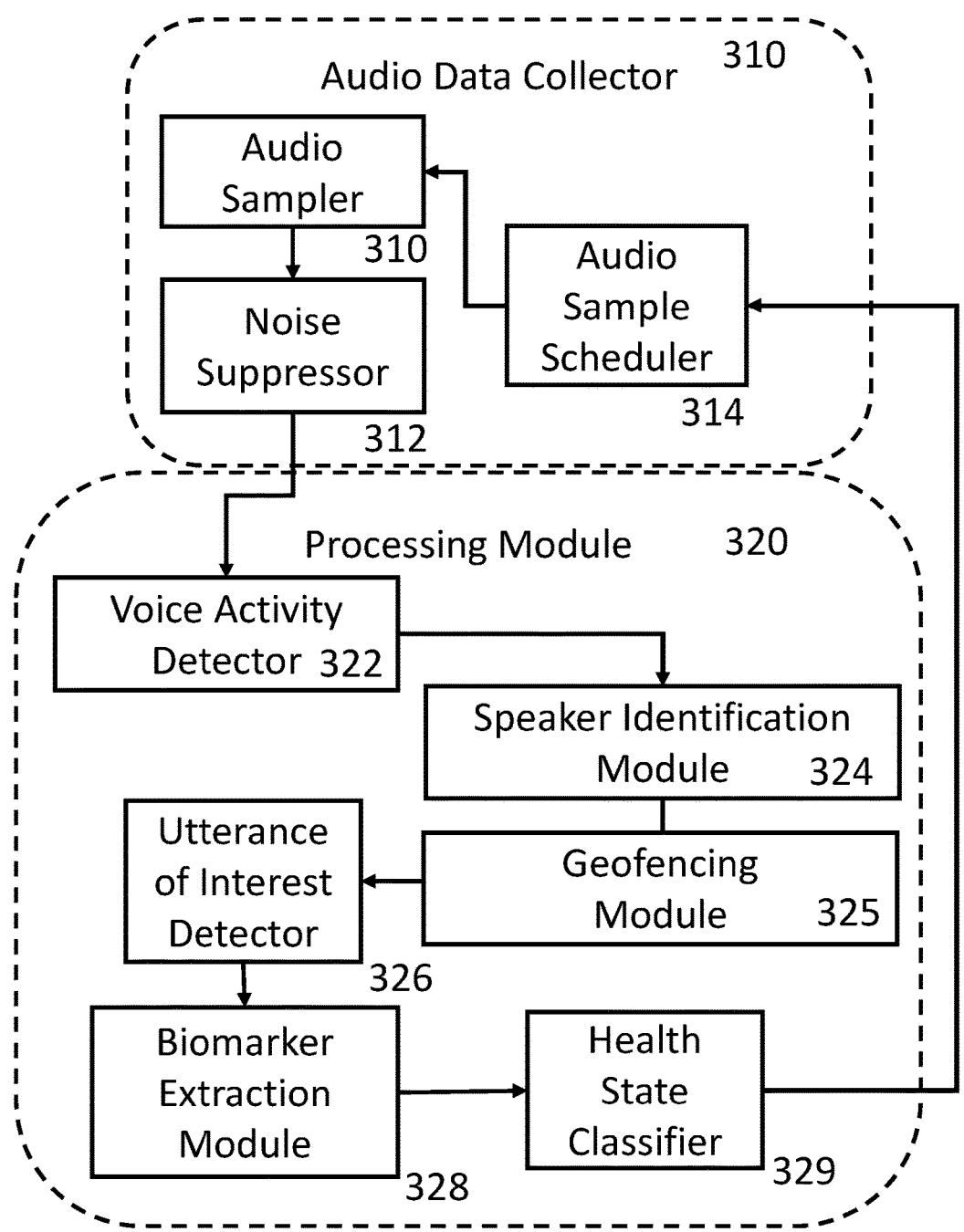
FIG. 3 a system for activating a cued health assessment according to another embodiment of the present inventions.

FIG. 3 shows another embodiment of the system 300 for activating a cued health assessment or a passive health assessment according to a classified health state or status of the user. As shown in FIG. 3, the audio data collector 310 can include an audio sampler 310 coupled to a noise suppressor 312. According to this embodiment, the audio sampler 310 is controlled by an embedded controller that embodies the audio sample scheduler 314. Here, rather than implementing the audio sample scheduler in the processing module 320, it is implemented directly in the hardware audio data collector 310. The audio sampler schedule 314 preferably receives activation and timing information from the processing module 310 (health state classifier 329). For example, when a user's health state is classified to be generally healthy, a passive health assessment is scheduled.

To activate a passive health assessment, the audio sampler 310 is "always on" and periodically collects a speech sample for voice biomarker extraction and health state classification by the processing module 320. Preferably, a noise suppressor 310 receives audio data from the audio sampler 310 and removes background noise and indoor reverberation from the audio data.

As shown in FIG. 3, the processing module 320 can include a voice activity detector 322, a speaker identification module 324, a geofencing module 325, an utterance of interest detector 326, a biomarker extraction module 328, and a health state classifier 329. According to the embodiment show in FIG. 3, preferably, a voice activity detection 322 is coupled to receive the noise-suppressed audio data. Preferably, a spectral content analysis is performed on the audio sample to determine that a speech sample is contained in the audio sample. Furthermore, it is preferable that a speaker identification module 324 is coupled to receive the voice-activity detected audio sample. In this manner, the audio sample can be validated to be a consented voice sample from an intentional user.

According to an embodiment the processing module 320 preferably includes a geofencing module 325 for determining a received voice sample as one that is collected from a predetermined location. Still preferable, according to an embodiment of present invention, an utterance-of-interest detector 326 determines a received voice sample as one that contains a predetermined utterance of interest by determining, according to one of plurality of biomarkers, that a received audio sample contains a predetermined utterance by matching the audio sample to a predetermined time-domain template.

Figure 4:
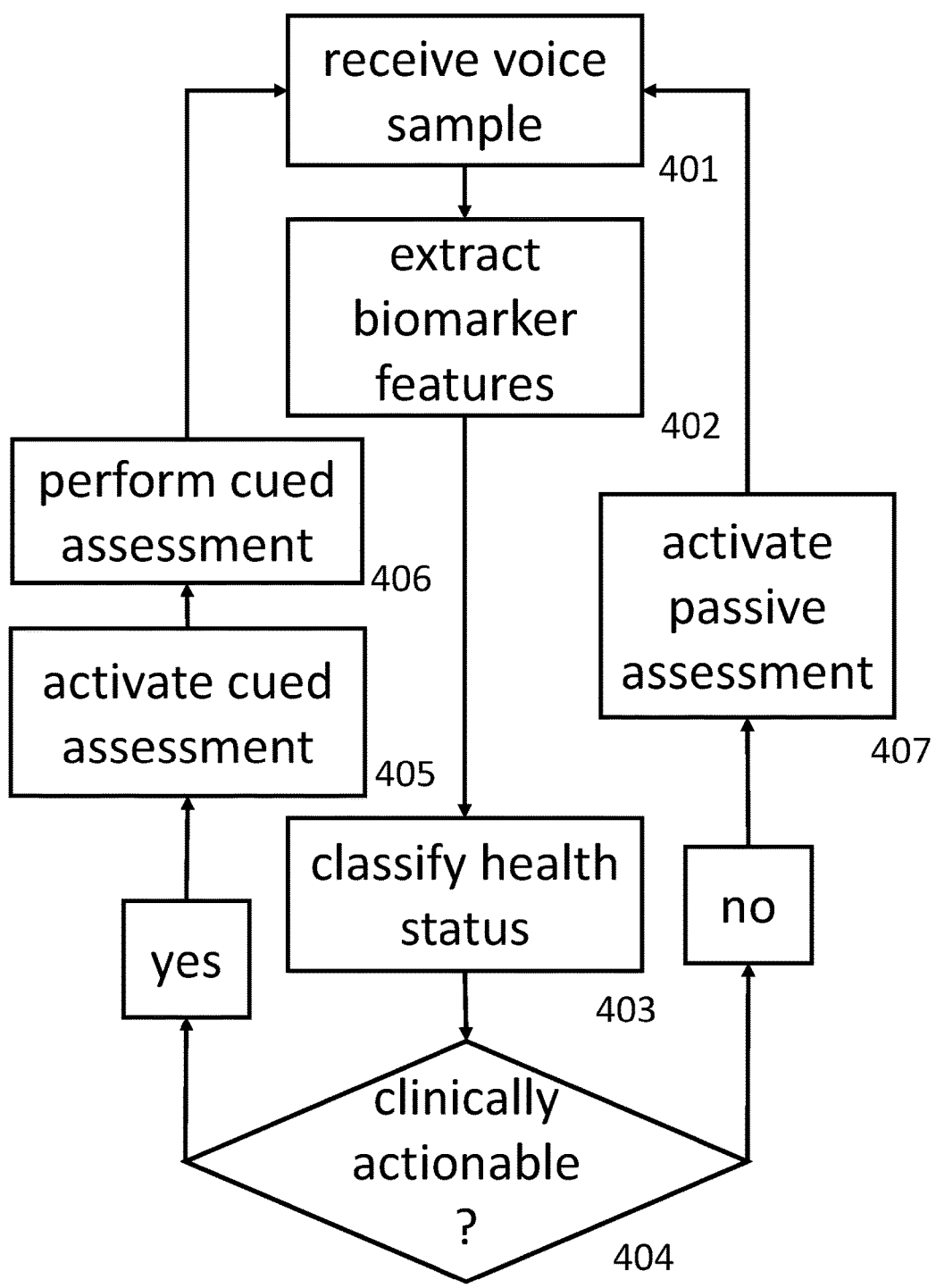
FIG. 4 depicts a method for activating a cued health assessment according to an embodiment of the present inventions.

FIG. 4 shows a method 400 for a method for activating a cued health assessment according to a classified a user state or status according to an embodiment of the present inventions. The method includes a step 401 of receiving voice samples from a continuous voice collection device, a step 402 of extracting one of a plurality of biomarkers from the received voice samples, a step 403 of classifying the received voice samples to one of plurality of predetermined health states according to the extracted biomarkers, and a step 405 of activating a cued health assessment module when the classified health state is a clinically actionable health state.

According to one embodiment of the method 400, the classified user status can be an emotional or affective state of the user, or the status can be a physiological state, along with a probability of the classification. As such, if the probability is determined to exceed a predetermined threshold (YES in FIG. 4), in step 404, a cued health assessment is activated and is provided to a user at step 406. According to another embodiment, if the probability of the classification is determined to not have exceed the predetermined threshold (NO in FIG. 4), the method 400 activates an passive assessment in step 407 to continuously capture speech samples.

According to an embodiment of the present invention, in step 403, a decision tree based method is implemented to perform the health state classification. For example of such tree-based classification method, see U.S. patent application Ser. No. 15/484,610, incorporated herein by reference.

In other embodiments, the classification can be performed with other established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Figure 5:
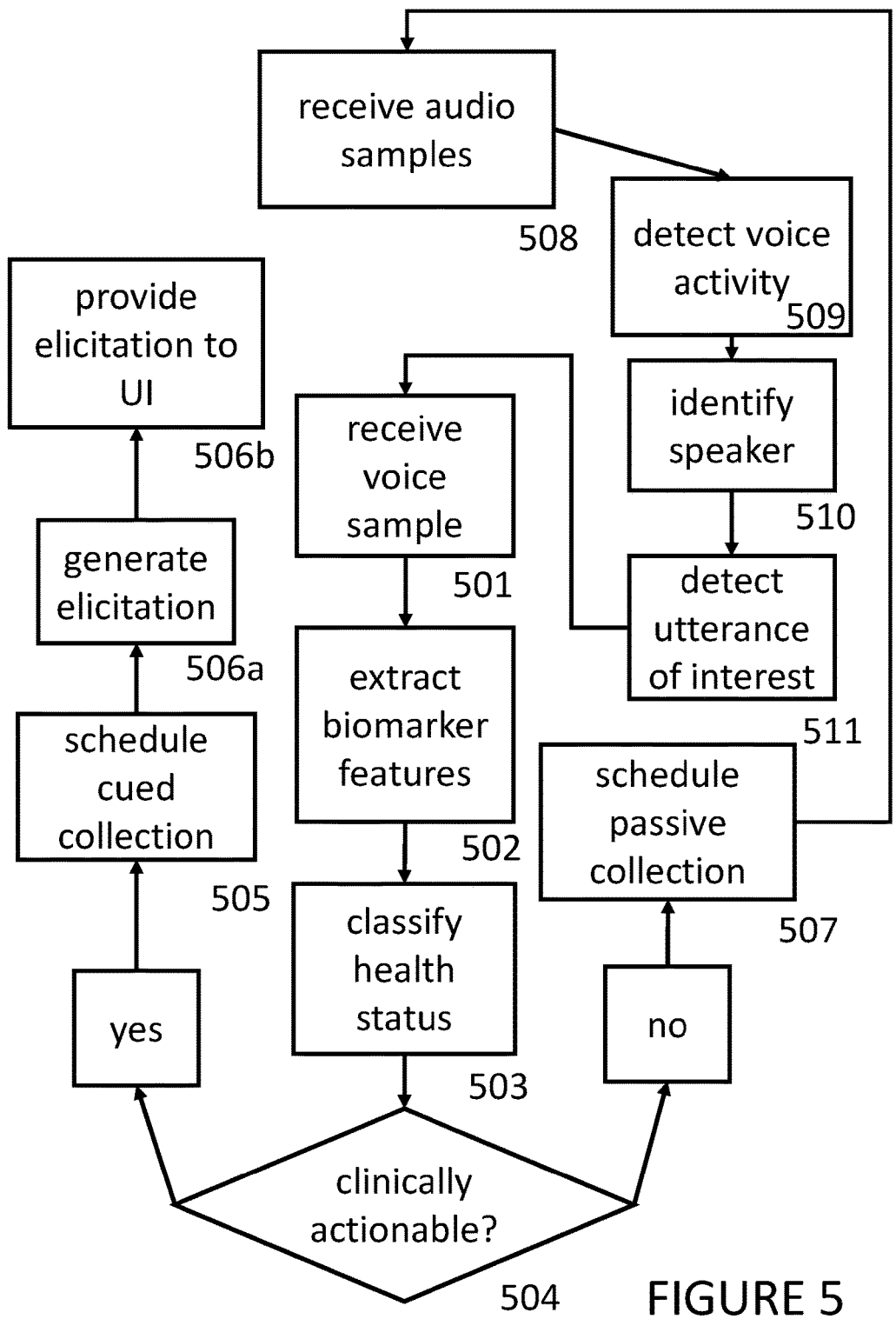
FIG. 5 depict a method for activating a passive health assessment according to an embodiment of the present inventions.

Next, FIG. 5 shows an embodiment of a method for activating a cued or passive health assessment, according to an embodiment. Preferably, the method includes a step 501 of receiving voice samples from a continuous voice collection device, a step 502 of extracting one of a plurality of biomarkers from the received voice samples, a step 503 of classifying the received voice samples to one of plurality of predetermined health states according to the extracted biomarkers, and a step 505 of activating a cued health assessment module when the classified health state is a clinically actionable health state (step 504). In particular, a user voice sample elicitation is generated in step 506a. A user voice sample elicitation can be provided through a text-to-voice interface or conventional user interfaces. In step 506b, the user elicitation is presented to the user in order to collect a voice sample from the user. After the user voice sample is received in step 501, in step 502, the voice biomarker extraction is repeated, and in step 503 the voice sample is analyzed and classified to determine the user's health state.

As shown in FIG. 5, when the user health state is classified as one that is not clinically actionable (no from step 504), a passive health assessment is activated. In step 507, a passive voice collection is scheduled. Preferably, the method includes a step 511 determining a received voice sample as one that contains a predetermined utterance of interest. Furthermore, the method determines a received voice sample as one that contains a predetermined utterance of interest by determining, according to one of plurality of biomarkers, that a received audio sample contains a predetermined utterance by matching the audio sample to a predetermined time-domain template.

Also shown in FIG. 5, the method preferably includes a step 509 of detecting a voice activity in a received audio sample by determining that the audio sample contains a predetermined amount of spectral content. Furthermore, the method preferably includes a step 510 of identifying the user as a consented user by determining, according one of a plurality of voice biometric features, that a received audio sample is collected from one of a predetermined speakers. Clinically Actionable Health States and Cued Digital Health Assessments.

In case of MDD, a ranked list of services can include, in case of a low risk status, 1) providing digital educational material, 2) providing care provider resources and referrals; 3) providing connections to support networks; in case of a medium risk status, 1) digital cognitive behavioral therapy, 2) a referral to clinical care, 3) a referral to a psychologist, psychiatrist, social worker, or counselor, 4) a recommendation to widely-used antidepressants such as SSRI; and in case of a high risk status, 5) a recommendation and direct referral to clinical intervention.

In the case of neurological disorder, including dementias, passive voice monitoring can enable cued health assessments. These can include, in case of a low risk status, providing 1) digital cognition assessments, for example, the Mini Mental State Examination, categorical fluency tests, 2) digital memory tests, e.g. Logical Memory test, 3) digital linguistic batteries, including naming, comprehension, and word-finding difficulty; in the case of medium risk status, providing 1) digital tests of ideational and constructional praxis, 2) a referral to a social worker, counselor, or neurologist; in the case of high risk status, 1) a recommendation and direct referral for a magnetic resonance imaging or positron emission tomography brain scan, 2) a recommendation and direct referral to clinical intervention.

In the case of respiratory disorder, including asthma, passive voice monitoring can enable cued health assessments. These can include, in case of a low risk status, providing 1) digital assessments such as the Asthma Control Test, 2) providing medication recommendations and availability alerts, 3) providing a referral to a social worker, counselor, or nurse; in the case of medium risk status, providing 1) referral for a lung function tests, including spirometry, 2) referral to a nurse or physician; in the case of high risk status, 1) connection to a physician or nurse via telephone, internet, or messaging, 2) referral to emergency medical services.

In the case of sleep disorder, including sleep apnea, passive voice monitoring can enable cued health assessments. These can include, in case of a low risk status, providing 1) digital questionnaires and assessments, 2) referrals for over-the-counter products including sleep aids or anti-snoring products, 3) referrals to digital insomnia cognitive behavioral therapies; in the case of medium risk status, providing 1) providing a referral to a social worker, counselor, or nurse, 2) referrals to wearable physiological monitors including respiration belt, photoplehtysmogram, 3) recommendations for prescription sleep products; in the case of high risk status, 1) referral for clinical sleep study, i.e. polysomnography, 2) connection to a physician or nurse via telephone, internet, or messaging, 3) recommendation for therapeutics including continuous positive airway pressure machine or other medical device

What is claimed is:

1. A system for activating a cued health assessment, the system comprising:
   a voice sample collector for receiving voice samples from a user, wherein the voice sample collector comprises a cued voice sample collector and a passive voice sample collector;
   a contextual data collector to collect additional contextual health data using one or more integrated sensors;
   an audio processing module comprising a voice biomarker extractor, a health state classification unit, and a voice sample scheduler;
   the voice biomarker extractor for extracting one of a plurality of acoustic features from the received voice samples;
   the health state classification unit for classifying the received voice samples to one of plurality of predetermined health states based on the acoustic features extracted by the voice biomarker extractor and the additional contextual health data collected by the integrated sensors; and
   the voice sample scheduler for activating a cued health assessment module when the classified health state is a clinically actionable health state, wherein the cued health assessment module performs the cued health assessment by providing a ranked list of services to the user.

2. The system of claim 1, wherein the integrated sensors comprise one or more of an accelerometer and a light sensor, and wherein the voice sample scheduler activates a passive health assessment module when the classified health state is not the clinically actionable health state.

3. The system of claim 1, wherein in the step of activating a cued health assessment module further comprises:
   activating an elicitation module according to a predetermined schedule to alert the user to provide the voice samples, collect the voice samples, and perform a cued health assessment by collecting user response to a set of predetermined survey questions.

4. The system of claim 1, further comprising:
   an utterance-of-interest detector for determining that the received voice samples contain a predetermined utterance of interest, from which the plurality of acoustic features can be extracted.

5. The system of claim 1, further comprising:
   a geofencing module for determining that the received voice samples are collected from a predetermined location.

6. The system of claim 1, further comprising:
   a voice activity detector for detecting a voice activity in a received audio sample by determining that the audio sample contains a predetermined amount of spectral content.

7. The system of claim 1, further comprising:
   a speaker identification module for determining that the received voice samples are collected from one of a predetermined speakers based on the plurality of acoustic features.

8. The system of claim 4, wherein the utterance-of-interest detector determines that the received voice samples contain the predetermined utterance of interest by matching the received voice samples to a predetermined time-domain template and comparing the plurality of acoustic features.

9. The system of claim 1, wherein the voice sample scheduler for activating a cued health assessment module schedules one of a digital voice collection exercise, a digitally administered health survey, and a telehealth session to be provided to the user.

10. The system of claim 1, wherein the health state classification unit of the audio processing module classifies the received voice samples to one of: depression, neurological, respiratory, and sleep disorders.

11. A method of activating a cued health assessment, the method comprising:
    receiving voice samples from a user, by a voice sample collector, wherein the voice sample collector comprises a cued voice sample collector and a passive voice sample collector;
    collecting additional contextual health data using one or more integrated sensors, by a contextual data collector;
    extracting one of a plurality of acoustic features from the received voice samples, by a voice biomarker extractor of an audio processing module;
    classifying the received voice samples to one of plurality of predetermined health states, by a health state classification unit of the audio processing module, based on the acoustic features extracted by the voice biomarker extractor and the additional contextual health data collected by the integrated sensors; and
    activating a cued health assessment module when the classified health state is a clinically actionable health state, by a voice sample scheduler of the audio processing module, wherein the cued health assessment module performs the cued health assessment by providing a ranked list of services to the user.

12. The method of claim 11, wherein the integrated sensors comprise one or more of an accelerometer and a light sensor, and wherein a passive health assessment module is activated when the classified health state is not a clinically actionable health state.

13. The method of claim 11, wherein in the step of activating a cued health assessment module further comprises:
activating an elicitation module according to a predetermined schedule to alert the user to provide the voice samples, collect the voice samples, and perform a cued health assessment by collecting user response to a set of predetermined survey questions.

14. The method of claim 11, further comprising:
determining that the received voice samples contain a predetermined utterance of interest, by an utterance-of-interest detector, and extracting the plurality of acoustic features from the predetermined utterance of interest.

15. The method of claim 11, further comprising:
determining that the received voice samples are collected from a predetermined location, by a geofencing module.

16. The method of claim 11, further comprising:
detecting a voice activity in a received audio sample, by a voice activity detector, wherein the voice activity detector determines that the audio sample contains a predetermined amount of spectral content.

17. The method of claim 16, further comprising:
determining that the received voice samples are collected from one of a predetermined speakers based on the plurality of acoustic features, by a speaker identification module.

18. The method of claim 14, wherein the utterance-of-interest detector determines that the received voice samples contain the predetermined utterance of interest by matching the received voice samples to a predetermined time-domain template and comparing the plurality of acoustic features.

19. The method of claim 11, wherein the step of activating a cued health assessment module comprises the voice sample scheduler scheduling one of a digital voice collection exercise, a digitally administered health survey, and a tele-health session to be provided to the user.

20. The system of claim 11, wherein the step of classifying the received voice samples comprises the health state classification unit of the audio processing module classifying the received voice samples to one of: depression, neurological, respiratory, and sleep disorders.

* * * * *